United States Patent [19]

Alderete et al.

[11] Patent Number: 5,714,121
[45] Date of Patent: Feb. 3, 1998

[54] OPTICAL CARBON DIOXIDE SENSOR, AND ASSOCIATED METHODS OF MANUFACTURE

[75] Inventors: Jason E. Alderete, Hopkins; Alan D. Olstein, St. Paul; Steven C. Furlong, Maple Grove, all of Minn.

[73] Assignee: Optical Sensors Incorporated, Minneapolis, Minn.

[21] Appl. No.: 535,878

[22] Filed: Sep. 28, 1995

[51] Int. Cl.$^6$ .................................. G01N 21/64
[52] U.S. Cl. ................... 422/82.07; 427/163.2; 427/2.13
[58] Field of Search .............. 422/82.05, 82.06, 422/82.07, 82.08, 82.09, 82.11; 436/68, 163, 172; 427/163.2, 2.13

[56] References Cited

U.S. PATENT DOCUMENTS

| | | | |
|---|---|---|---|
| 4,889,407 | 12/1989 | Markle et al. | 422/82.11 X |
| 4,892,383 | 1/1990 | Klainer et al. | |
| 4,919,891 | 4/1990 | Yafuso et al. | |
| 5,006,314 | 4/1991 | Gourley et al. | |
| 5,098,659 | 3/1992 | Yim et al. | |
| 5,280,548 | 1/1994 | Atwater et al. | |
| 5,330,718 | 7/1994 | Hui et al. | |
| 5,462,880 | 10/1995 | Kane et al. | 422/82.07 X |

OTHER PUBLICATIONS

Hirschfeld et al., "Laser–Fiber–Optic Optrode for real Time In Vivo Blood Carbon Dioxide Level Monitoring" *J. Lightwave Tech.* 5(7):1027–1033, (1987).

Petersen et al., "Fiber–Optic Sensors for Biomedical Applications," *Science* 224(4645):123–127 (1984).

Vurek et al., "A Fiber Optic $PCO_2$ Sensor," *Annals of Biom. Eng.* 11:499–510 (1983).

Auer, P.D. et al. "The effect of antioxidant/quenchers and a fluorescent whitening agent on the quantum yield of photoinduced degradation of tryptophan in a rigid, oxygen–permeable medium" J. Photochem. Photobiol. vol. 86, (1995) pp. 267–273.

Longin, A. et al. "Comparison of anti–fading agents used in fluorescence microscopy" J. Histochem. Cytochem. vol. 41, (1993) pp. 1833–1840.

Valnes, K. et al. "Retardation of immunofluorescence fading during microscopy" J. Histochem. Cytochem. vol. 33 (1985) pp. 755–761.

*Primary Examiner*—Jeffrey Snay
*Attorney, Agent, or Firm*—Dianne E. Reed; Bozicevic & Reed LLP

[57] ABSTRACT

A method is provided for manufacturing a fiber optic sensor for detecting or measuring the concentration of carbon dioxide in a sample fluid. The method involves incorporation of a fluorescent indicator composition in a silicone capsule slidably arranged over the tip of a fiber optic, sealed with a suitable adhesive. To amplify the detectable signal obtained, the capsule is preferably fabricated so as to contain reflective particles, and tapers to a narrow tip. Novel optical sensors, manufactured using the aforementioned method, are provided as well.

26 Claims, 1 Drawing Sheet

OPTICAL CARBON DIOXIDE SENSOR, AND ASSOCIATED METHODS OF MANUFACTURE

TECHNICAL FIELD

The present invention relates generally to optical sensors for monitoring a parameter of interest in a sample. More particularly, the invention relates to a fiber optic sensor for detecting and quantitating carbon dioxide in a sample fluid such as blood. Methods for manufacturing the novel sensors are provided as well.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," Analytical Chemistry 56(1):16A–34A (1984), each of which is incorporated by reference herein.

Publications such as these generally illustrate that it is known to integrate a chemical sensor with a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to provide especially sensitive remote monitoring capabilities. Chemical sensor compositions that are incorporated at the distal end of fiber optic sensors are often configured as membranes that are secured at the distal tip of the waveguide device or optrode.

Gas sensors of this general type are useful in monitoring gas concentrations such as oxygen and carbon dioxide in bloodstreams and the like. Also, it is sometimes desirable to provide sensors that monitor other parameters such as pH. Other ion concentrations can also be detected, such as potassium, sodium, calcium and metal ions.

A typical fiber optic sensor device positions the sensor material at a generally distal location with the assistance of one or more types of support means. Support means must be such as to permit interaction between a parameter-sensitive indicator—e.g., a fluorescent dye or the like—and the substance being subjected to monitoring, measurement and/or detection.

Quantitative analysis of carbon dioxide has traditionally been accomplished through the use of infrared spectroscopy and electrochemical techniques. Infrared spectroscopy relies on the strong absorption by carbon dioxide in the 4.2–4.4 μm region. Conventional electrochemical carbon dioxide sensors utilize an indirect approach in the determination of the analyte. In the conventional carbon dioxide electrode, a carbon dioxide permeable membrane serves as a barrier between the sample and an electrolyte-containing reservoir. A pH electrode is placed in the reservoir. Carbon dioxide, when dissolved in the aqueous buffer, alters the chemical equilibrium of the buffer. Additional dissolved carbon dioxide lowers the pH of the buffer via the formation of carbonic acid. This pH change in the buffer reservoir is detected with the pH electrode.

Such electrochemical sensors require frequent recalibration as the electrolyte must be replenished. These sensors are generally not suitable for single patient usage due to complexity and size.

Carbon dioxide sensing optrodes have been also been disclosed which embody a similar strategy, and have been described, for example, by Hirschfeld et al., in "Laser-Fiber-Optic 'Optrode' for Real Time In Vivo Blood Carbon Dioxide Level Monitoring," *Journal of Lightwave Technology* LT-5(7):1027–1033 (1987). These optrodes sense changes in pH underneath an ion-impermeable membrane by employing a pH-sensitive dye which changes either its absorbance or fluorescence in response to fluctuations in environmental $CO_2$. While these prior sensors are effective in detecting and quantitating carbon dioxide, there nevertheless remains a need in the art for improved devices useful in measuring carbon dioxide concentration in sample fluids.

The present invention provides such sensors. The novel sensors have a carbon dioxide permeable capsule filled with a fluorescent indicator at the distal end of an optical fiber. The fluorescent indicator is excited by light conducted through the optical fiber, with the fluorescence emission of the indicator monitored through the optical fiber as well. As carbon dioxide enters the capsule, carbonic acid is formed therein, resulting in a lower pH. The pH change causes a shift in the fluorescence of the indicator, which is detected instrumentally through the fiber optic.

The novel sensors are simple and inexpensive to manufacture, can be substantially scaled down in terms of size, and can be made such that the detectable signal obtained is significantly enhanced.

Pertinent Art

In addition to the references mentioned in the preceding section, the following relate to fiber optic sensors for monitoring carbon dioxide, and as such may be of background interest to the present invention:

U.S. Pat. No. 4,892,383 to Klainer et al. describes fiber optic chemical sensors stated to be useful, inter alia, in monitoring trichloroethylene vapor and total organic chloride content of groundwater. The sensors have a reservoir cell body containing an indicator reagent separated from the sample undergoing analysis by a semi-permeable, i.e., analyte-selective, membrane.

U.S. Pat. No. 4,919,891 to Yafuso et al. describes a fiber optic sensor in which an indicator composition is encased in a cellulosic overcoat stated to protect and enhance the signal obtained.

U.S. Pat. No. 5,006,314 to Gourley et al. describes fiber optic sensors in which a relatively rigid sleeve means is positioned at the sensor tip, capped by an analyte-permeable membrane so as to enclose an indicator composition, in turn comprising a dye dispersed in a polymeric matrix.

U.S. Pat. No. 5,098,659 to Yim et al. discloses a fiber optic probe which can in one embodiment be used to measure carbon dioxide concentration in a sample. A pellet containing a first indicator is disposed at the fiber tip, covered with a reflective material such as gold foil, along with a polymeric matrix containing a second indicator, which may represent a coating encasing the foil-covered pellet.

U.S. Pat. No. 5,280,548 to Atwater et al. relates to a fiber optic sensors for analyzing pH and carbon dioxide in liquids.

For $pCO_2$ monitoring, a fiber optic sensor is provided which is coated on its distal end with a carbon dioxide sensitive fluorescent dye-polymeric-silicone elastomeric matrix.

U.S. Pat. No. 5,330,718 to Hui et al. relates to a sensor element for incorporation in a fiber optic sensing device. The element includes an analyte-permeable matrix which supports an indicator solution of an analyte-sensitive dye contained in a plurality of vesicles dispersed throughout the matrix.

Peterson et al.,"Fiber Optic Sensors for Biomedical Applications," *Science* 224 (4645):123–127 (1984) and Vurek et al., "A Fiber Optic $pCO_2$ Sensor," *Annals of Biomedical Engineering* 11:499–510 (1983) describe carbon dioxide sensors having a silicone rubber tube filled with an indicator solution present at the distal end of an optical fiber.

Although these references relate to fiber optic sensors stated to be useful in the measurement of carbon dioxide concentration in sample fluids, they do not describe a manufacturing method or sensor as disclosed and claimed herein, nor are the advantages of the present invention achieved.

SUMMARY OF THE INVENTION

Accordingly, it is a primary object of the invention to address the above-mentioned needs in the art by providing a novel process for making a fiber optic sensor useful in the detection and quantitation of carbon dioxide in sample fluids, and to provide novel optical optic carbon dioxide sensors using the novel method.

Additional objects, advantages and novel features of the invention will be set forth in part in the description which follows, and in part will become apparent to those skilled in the art upon examination of the following, or may be learned by practice of the invention.

In one aspect, a method for making an optical $CO_2$ sensor is provided which involves: (a) providing an open-ended capsule of a $CO_2$-permeable silicone material; (b) filling the capsule with an indicator solution containing a pH-sensitive indicator component; (c) providing an optical fiber having a distal tip for contacting a sample fluid, and a proximal region for communication with means for receiving a signal from the distal tip; (d) slidably arranging the capsule over the distal tip such that the capsule is arranged upon the fiber at a predetermined position with indicator solution retained therein, forming a sensor chamber; and (e) affixing the capsule on the distal tip using a sealing means capable of providing a liquid-tight seal. The method may further involve incorporation of reflective particles or other materials into the silicone cap, and/or forming the capsule into a predetermined geometry prior to filling with indicator solution.

In another aspect, novel carbon dioxide sensors are provided which are made using the aforementioned method.

BRIEF DESCRIPTION OF THE DRAWINGS

In the course of this description, reference will be made to the attached drawing, wherein.

DETAILED DESCRIPTION OF THE INVENTION

Figure 1:
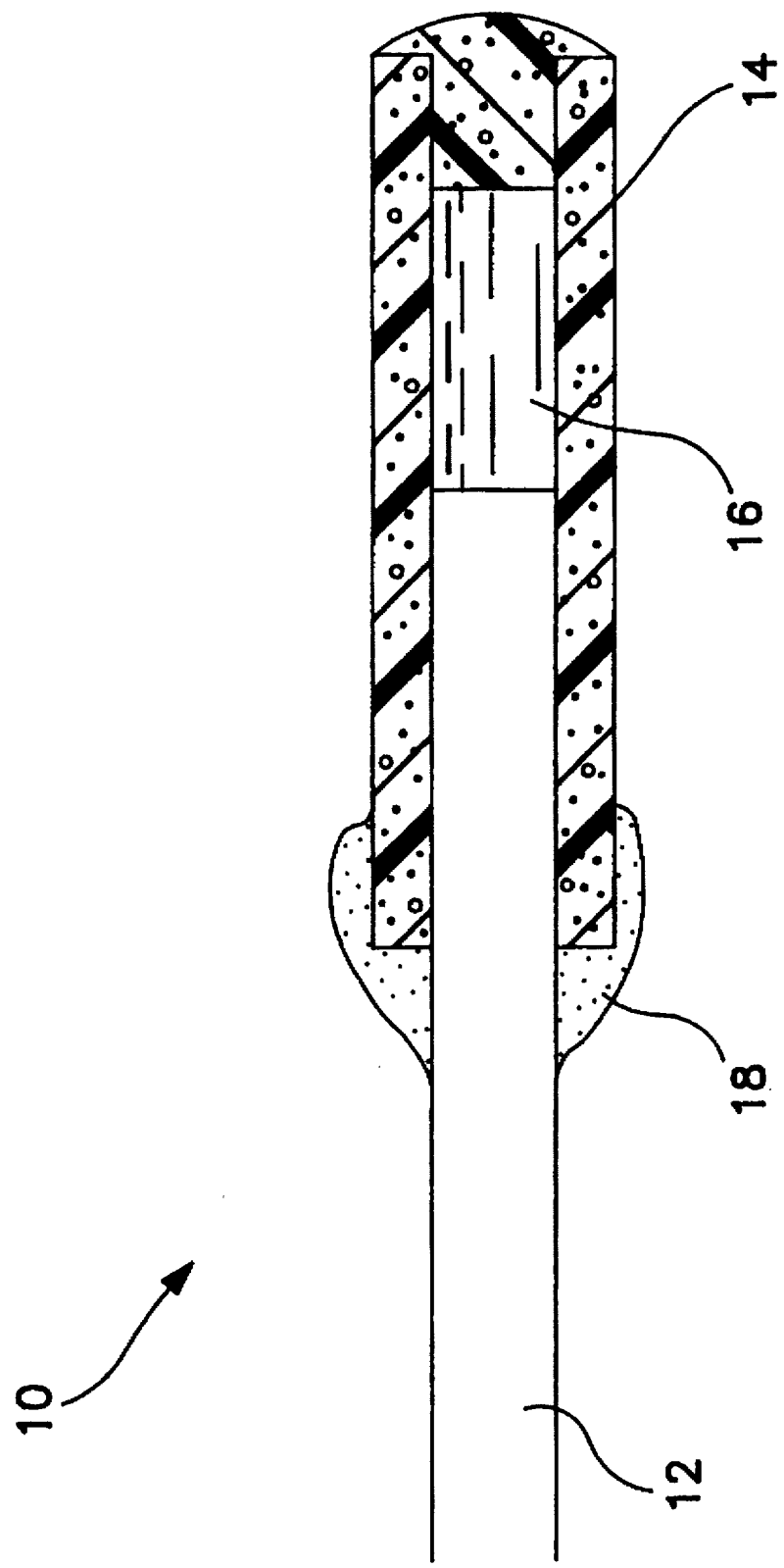
FIG. 1 is a generally schematic view of the sensing tip of a fiber optic device manufactured according to the method of the present invention.

Before the present sensors and methods are disclosed and described, it is to be understood that this invention is not limited to specific sensor formats or materials, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an indicator material" includes mixtures of suitable indicator materials, reference to "a reflective material" includes mixtures of two or more reflective materials, and the like.

In describing and claiming the present invention, the following terminology will be used in accordance with the definitions set out below.

The term "sample fluid" as used herein refers to a liquid or gaseous material which may be analyzed using the presently disclosed sensors. Generally, "sample fluids" analyzed using the sensors manufactured herein will be physiological fluids such as blood.

The term "indicator" as in "indicator composition," "indicator material" or "indicator component" refers to a species which is sensitive to the parameter of interest in the sample fluid undergoing analysis, i.e., carbon dioxide concentration.

The terms "reference material" or "reference dye" intends a species which is substantially insensitive to the parameter of interest in the sample fluid undergoing analysis, i.e., carbon dioxide concentration, and will be used in conjunction with an indicator material.

At the outset, an optical fiber means is provided which serves to communicate optical signals from a sample fluid to a detection means. The optical fiber means will typically comprise a single elongated optical fiber, although it may comprise a bundle of optical fibers associated in parallel.

Examples of suitable fiber substrate materials include glass, plastic, glass/glass composite and glass/plastic composite fiber waveguides. A critical characteristic of optical fibers is attenuation of the optical signal. Thus, glasses which contain unacceptable levels of transition-metal impurities when prepared from naturally occurring materials lead to high absorption losses. Silica fibers of acceptable quality can be prepared from purified starting materials (e.g., silicon tetrachloride and germanium tetrachloride) using conventional glass-melting techniques of drawing into fibers.

Generally, although not necessarily, the fiber will be provided with a cladding means. As will be appreciated by those skilled in the art, the cladding means serves to provide structural support for an otherwise fragile fiber, and also provides a coating which guides light conducted along the fiber. In the present case, the cladding means typically comprises a fluoropolymer such as polymeric fluoroacrylate. However, the cladding means may also be comprised of glass, or it may be comprised of polystyrene, polyimide or any other suitable plastic material.

Prior to affixing the indicator-containing silicone capsule thereon, the fiber tip may, if desired, be pretreated, for example, by rinsing or washing, or by activation using any number of techniques (e.g., corona, plasma, etching, or the like). Other surface treatment methods may also be used if desired.

The capsule to be used in housing the indicator composition is comprised of silicone. The silicone may be obtained commercially from any number of sources, or it may be synthesized in a suitable mold using techniques well-known to those skilled in the art of polymer chemistry. One such technique, as will be appreciated by those working in the field, involves hydrolysis of alkylsilicon or arylsilicon halides. An alternative technique involves base-catalyzed ring-opening polymerization of cyclic siloxanes, optionally followed by crosslinking, effected by cohydrolysis with alkyltrichlorosilanes or by treatment with peroxides or oxygen. Many other methods are known as well, and can be used in conjunction with the present invention.

The capsule is of a configuration and diameter so as to provide a liquid-tight seal. It may be desirable to mold or form the silicone capsule prior to use in the present method. Preferably, molding or forming involves tapering the capsule such that the open end which is slid over the fiber tip tapers gradually to a narrow tip. Such a configuration increases the detectable signal obtained. While not wishing to be bound by theory, it is believed that such a tapered capsule serves functions as an optical condenser to amplify the emission light returning from the sample fluid undergoing analysis. Generally, the tapered configuration is obtained by preparing the silicone capsule in a mold suitably shaped, as alluded to above.

It may also be desirable to incorporate a reflective material into the sensor. The reflective material may be incorporated into the silicone cap, or it may be suspended as a homogeneous dispersion in the indicator solution. In the former case, particles of a selected reflective material are admixed with the silicone precursors (i.e., the reactants used to provide the final silicone material) during manufacture of the cap. Suitable reflective materials include titanium dioxide, zinc oxide and barium sulfate, with titanium dioxide particularly preferred. Generally, the silicone capsule so prepared will contain on the order of 0.01 wt.% to 20 wt.% reflective material, preferably in the range of about 0.1 wt.% to 10 wt.%, most preferably in the range of about 1 wt.% to 10 wt.%. If the reflective material is incorporated into the indicator solution rather than the silicone capsule, generally about 1 wt.% to 10 wt.% reflective material will be suspended as a homogeneous dispersion therein. Particle size is not critical, but will generally be on the order of approximately 0.1 to 100 µm in diameter, preferably on the order of approximately 1 µm to 20 µm in diameter, and most preferably on the order of approximately 1 µm to 5 µm in diameter. When the reflective material is incorporated in the indicator solution, smaller particles are preferred, normally on the order of 1 µm or smaller; larger particles can be incorporated into the silicone capsule, but generally particles less than about 100 µm in diameter are preferred.

Once obtained or manufactured, the silicone capsule is filled with an indicator solution, preferably although not necessarily under vacuum. The indicator solution is prepared by incorporating a pH-sensitive indicator material into an aqueous solution, typically purified water buffered to a pH in the range of about 6.5 to 9.0, preferably in the range of about 7.0 to 8.5, using any suitable buffering media. As will be appreciated by those skilled in the art, suitable buffering solutions may be readily prepared or are commercially available from a number of sources. Examples of specific buffering solutions which may be used include alkali metal salts of bicarbonate anion (e.g., sodium bicarbonate), 1,4-piperazinediethane-sulfonic acid (PIPES), 3-(N-morpholino)propanesulfonic acid (MOPS), N-tris (hydroxymethyl)methyl-3-aminopropane-sulfonic acid (TAPS) and N-tris(hydroxymethyl)methyl-2-aminoethanesulfonic acid (TES). The pH-sensitive indicator material will generally be a fluorescent dye, typically although not necessarily selected from the group consisting of fluorescein, carboxyfluorescein, fluorescein polyacrylamide copolymer, fluorescein isothiocyanate polymer conjugates, coumarin, seminaphtharhodafluorescein, seminaphthafluorescein, naphthafluorescein, hydroxypyrene trisulfonic acid (HPTS), dichlorofluorescein, and fluorescein salts such as lithium fluoresceinate. The indicator solution will typically contain on the order of about 0.01 wt.% to 1.0 wt.% fluorescent dye.

It may also be desirable to incorporate a reference dye into the indicator solution. The reference dye is selected such that is substantially insensitive both to the presence or concentration of carbon dioxide in the sample fluid undergoing analysis, and to internal pH shifts in the indicator solution (i.e., shifts in pH which do not correspond to $CO_2$ concentration). Suitable reference dyes which may be used in conjunction with the present invention are readily available commercially, and include, but are not limited to, rhodamine, carboxytetramethyl-rhodamine, Cascade Blue, Lucifer Yellow, and Texas Red. The indicator solution will generally contain on the order of about 0.1 wt.% to about 1.0 wt.% wt.% reference dye.

Other components may be incorporated into the indicator composition as well, typically any materials that are compatible with the indicator, the silicone cap, and the fiber or cladding material. One preferred additive is a singlet oxygen quencher such as diazabicyclo(2.2.2)octane (DABCO), which has been found to significantly reduce photodecay during sensor illumination. Generally, in the range of approximately 0.05 wt.% to 0.5 wt.% DABCO or an equivalent singlet oxygen quencher will be included in the indicator solution. Other components such as surfactants, antioxidants and ultraviolet stabilizers may also be present in the indicator composition.

The silicone capsule having indicator solution therein is then carefully slid onto the optical fiber tip, preferably in the indicator solution itself, so as to avoid introduction of air bubbles into the solution. The interface between the capsule and the fiber or cladding surface is then sealed using a suitable adhesive, and the adhesive is then cured.

Examples of preferred adhesive materials include, but are not limited to, polyurethanes, acrylates, epoxy resins, acrylated epoxy resins, and silicones. Moisture-curable adhesives are particularly preferred, although radiation curable materials or heat-curable adhesives may be used as well.

Examples of specific commercially available adhesives which can be used to seal the capsule on the fiber tip include silicone rubber compounds, particularly room-temperature-vulcanizing (RTV) silicone rubbers, such as available from D Aircraft Products, Inc. (as Dapcocast®), Hüls America, Inc./Petrarch Systems, Miles Inc. Industrial Chemicals Divisional (as BAYSILONE® RTV I and RTV II), PPG Industries, Specialty Chemicals, and Wacker Silicones Corp.

One embodiment of a sensor manufactured using the technique of the present invention is shown in FIG. 1. The sensor is shown generally at 10, with the optical fiber 12 capped with silicone capsule 14 housing indicator solution 16. Adhesive material 18 seals the interface between fiber 12 and capsule 14.

In use, the distal end of the sensor so prepared is immersed in a sample fluid, and light of a predetermined wavelength is directed from an external source, through the optical fiber, impinging distally on the encapsulated indicator composition. The intensity of the emitted fluorescent light returning along the fiber is directly related to the concentration of carbon dioxide in the sample, as a result of the pH-sensitive indicator material present at the fiber tip (i.e., the pH of the indicator solution is directly related to carbon dioxide concentration, as a result of carbonic acid formation). The emitted light is carried by the optical fiber to a device where it is detected and converted electronically to a $CO_2$ concentration value. When a reference dye is present in the indicator composition, the intensity of light emitted therefrom may be used to compensate, via ratioing, the signal obtained from the indicator.

It will be appreciated by those working in the art that sensors fabricated using the presently disclosed and claimed techniques may be used in a wide variety of contexts. That is, while the invention has primarily been described in conjunction with the measurement of carbon dioxide concentration in blood, the sensors fabricated using the present method may be used to evaluate any number of sample types in a variety of industries, including fermentation technology, cell culture, and other biotechnology applications.

Thus, it is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

Experimental

The following examples are put forth so as to provide those of ordinary skill in the art with a complete disclosure and description of how to make and use the compounds of the invention. Efforts have been made to ensure accuracy with respect to numbers (e.g., amounts, temperature, etc.) but some deviation and deviations should be accounted for. Unless indicated otherwise, parts are parts by weight, temperature is in ° C. and pressure is at or near atmospheric.

All solvents were purchased as HPLC grade and, where appropriate, solvents and reagents were analyzed for purity using common techniques.

Materials and reagents were obtained as follows: HCN plastic clad fibers, from Spectran Specialty Optics Co.; Silastic® silicone rubber tubing, from Dow Corning; and silicone RTV adhesive, from Loctite; (Newington, Conn.). Lithium fluoresceinate was prepared from the acid form of fluorescein by dissolving the dye into a mixture of water and methanol in the presence of LiOH, and precipitating the salt with acetone.

Example 1

200 µm core HCN plastic clad fibers were connectorized (ST) and used without chemical pretreatment. Silastic® rubber tubing, 0.012" i.d.×0.025" o.d., was obtained from Dow Corning. The tubing was filled with a solution of buffer and lithium fluoresceinate (0.5 mM or 5.0 mM PIPES, 0.14 m, 40 µg/mL, $1.2 \times 10^{-4}$M lithium fluoresceinate, pH 7.4), under vacuum. The tubing was slid over the cleaved fiber end and sealed with silicone RTV 25% w/w (obtained from Loctite Corp.) in methylene chloride, and cured at room temperature for 4 hours.

The sensor so prepared was tested using buffer tonometry at 37° C. under standard conditions, to examine operational signal loss and capability of determining variable levels of carbon dioxide. The sensors were found to be highly sensitive and responded rapidly.

Similar results were obtained when sensors were prepared as just described, but using an indicator solution containing 8 mM bicarbonate buffer with $5 \times 10^{-5}$ mM HPTS and 144 mM NaCl.

Example 2

The procedure of Example 1 was followed, but 0.1 wt. % DABCO was incorporated in the indicator solution. This appeared to substantially reduce photodecay during sensor illumination. A first sensor prepared with DABCO gave a calculated drift rate of 0.788%/hr, while the same sensor without DABCO gave a calculated drift rate of 11.7%/hr.

Example 3

The procedure of Example 1 is followed, but 2.0 wt. % titanium dioxide (particle size<1 µm) is incorporated in the indicator solution. This will be found to increase the signal obtained upon measurement of carbon dioxide in samples undergoing analysis.

Example 4

The procedure of Example 1 is followed, but 2.0 wt. % titanium dioxide (particle size>100 µm) is incorporated in the silicone capsule. This will be found to increase the signal obtained upon measurement of carbon dioxide in samples undergoing analysis.

Example 5

The procedure of Example 1 is followed, but the silicone capsule which is used to encapsulate the indicator solution is tapered. As with incorporation of titanium dioxide particles in either the indicator solution (as in Example 3) or the capsule material (as in Example 4), the tapered capsule will be found to increase the signal obtained upon measurement of carbon dioxide in samples undergoing analysis.

We claim:

1. A method for making an optical $CO_2$ sensor having a distal end for contacting a sample fluid and a proximal region for communication with means for receiving an emitted fluorescent signal, the method comprising the steps of: (a) providing a capsule of a $CO_2$-permeable silicone material; (b) filling the capsule with an indicator solution containing a pH-sensitive indicator component; (c) providing a single optical fiber having a distal tip and a proximal region for communication with means for receiving a signal from the distal tip; (d) slidably arranging the capsule over the distal tip such that the capsule is arranged upon the fiber at a predetermined position with indicator solution retained therein, forming a sensor chamber, and wherein said arranging is carried out in the indicator solution, thereby avoiding introduction of air bubbles into the sensor chamber; and (e) affixing the capsule on the distal tip using a sealing means capable of providing a liquid-tight seal.

2. The method of claim 1, wherein the capsule is tapered to amplify the signal received from the distal tip.

3. The method of claim 1, wherein the sealing means comprises a deposit of an adhesive composition curable by light, moisture and/or heat.

4. The method of claim 3 wherein the adhesive composition comprises a moisture-curable RTV silicone rubber.

5. The method of claim 1, wherein the indicator component is a fluorescent dye.

6. The method of claim 5, wherein the indicator solution further comprises at least one additional component selected from the group consisting of surfactants, antioxidants, and ultraviolet stabilizers.

7. The method of claim 5, wherein the indicator solution further comprises a singlet oxygen quencher.

8. The method of claim 5, wherein the indicator solution additionally contains a reference dye substantially insensitive to the presence of $CO_2$ and internal shifts in pH.

9. The method of claim 5, wherein the fluorescent dye is selected from the group consisting of fluorescein, carboxyfluorescein, fluorescein polyacrylamide copolymer, fluorescein isothiocyanate polymer conjugates, coumarin, seminaphtha-rhodafluorescein, seminaphthafluorescein, naphtha-fluorescein, hydroxypyrene trisulfonic acid, dichlorofluorescein, and alkali metal fluorescein salts.

10. The method of claim 9, wherein the fluorescent dye is hydroxypyrene trisulfonic acid.

11. The method of claim 1, wherein the capsule contains particles of a reflective material dispersed therein.

12. The method of claim 11, wherein the reflective material is selected from the group consisting of titanium dioxide, zinc oxide and barium sulfate.

13. The method of claim 12, wherein the reflective material is titanium dioxide.

14. A fiber optic sensor for determining the concentration of carbon dioxide in a sample fluid, wherein the sensor has a distal end for contacting a sample fluid and a proximal region for communication with means for receiving an emitted flourescent signal, the sensor comprising: (a) a single optical fiber having a distal tip and a proximal region for communication with means for receiving a signal from the distal tip, wherein light of a predetermined wavelength may be directed through the optical fiber towards the distal tip, and emitted fluorescent light returns along the fiber to be detected and converted to a carbon dioxide concentration value; (b) a capsule arranged over the distal tip at a predetermined position, comprised of a $CO_2$-permeable silicone material; (c) an indicator solution retained within the capsule having a pH-sensitive indicator component therein and containing substantially no air; and (d) a sealing means affixing the capsule on the distal tip, such that a liquid-tight seal is provided.

15. The sensor of claim 14, wherein the capsule is tapered to amplify the signal received from the distal tip.

16. The sensor of claim 14, wherein the sealing means comprises a deposit of an adhesive composition curable by light, moisture and/or heat.

17. The sensor of claim 16, wherein the adhesive composition comprises a moisture-curable RTV silicone rubber.

18. The sensor of claim 14, wherein the indicator component is a fluorescent dye.

19. The sensor of claim 18, wherein the indicator solution further comprises at least one additional component selected from the group consisting of surfactants, antioxidants, and ultraviolet stabilizers.

20. The sensor of claim 18, wherein the indicator solution further comprises a singlet oxygen quencher.

21. The sensor of claim 18, wherein the indicator-solution additionally contains a reference dye substantially insensitive to the presence of $CO_2$ and internal shifts in pH.

22. The sensor of claim 18, wherein the fluorescent dye is selected from the group consisting of fluorescein, carboxyfluorescein, fluorescein polyacrylamide copolymer, fluorescein isothiocyanate polymer conjugates, coumarin, seminaphtharhodafluorescein, seminaphthafluorescein, naphtha-fluorescein, hydroxypyrene trisulfonic acid, dichlorofluorescein, and alkali metal fluorescein salts.

23. The sensor of claim 22, wherein the fluorescent dye is hydroxypyrene trisulfonic acid.

24. The sensor of claim 14, wherein the capsule contains particles of a reflective material dispersed therein.

25. The sensor of claim 24, wherein the reflective material is selected from the group consisting of titanium dioxide, zinc oxide and barium sulfate.

26. The sensor of claim 25, wherein the reflective material is titanium dioxide.

* * * * *